United States Patent
Kamal et al.

(10) Patent No.: US 7,189,710 B2
(45) Date of Patent: Mar. 13, 2007

(54) C2-FLUORO PYRROLO [2,1-C][1,4]BENZODIAZEPINE DIMERS

(75) Inventors: Ahmed Kamal, Hyderabad (IN); Peram Surakattula Murali Mohan Reddy, Hyderabad (IN); Depatla Rajashekhar Reddy, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 305 days.

(21) Appl. No.: 10/812,840

(22) Filed: Mar. 30, 2004

(65) Prior Publication Data

US 2005/0222131 A1    Oct. 6, 2005

(51) Int. Cl.
C07D 519/00    (2006.01)
A61K 31/55    (2006.01)
A61P 35/00    (2006.01)
A61P 35/02    (2006.01)

(52) U.S. Cl. ...................................... 514/220; 540/496
(58) Field of Classification Search ................ 540/496; 514/220

See application file for complete search history.

(56) References Cited

FOREIGN PATENT DOCUMENTS

WO    9318045    9/1993

OTHER PUBLICATIONS

Gregson et al., Stephen J. "Design, Synthesis, and Evaluation of a Novel Pyrrolobenzodiazepine DNA-Interactive Agent with Highly Efficient Cross-Linking Ability and Potent Cytotoxicity." J. Med. Chem.. (2001), 44, pp. 737-748.

Thurston et al., David E. "Synthesis of Sequence-Selective C8-Linked Pyrrolo[2,1-c][1,4]benzodiazepine DNA Interstrand Cross-Linking Agents." J. Org. Chem. (1996), 61, pp. 8141-8147.

Kamal et al., Ahmed "Design, Synthesis, and Evaluation of New Noncross-Linking Pyrrolobenzodiazepine Dimers with Efficient DNA Binding Ability and Potent Antitumor Activity." J. Med. Chem. (2002), 45, 4679-4688.

*Primary Examiner*—Bruck Kifle
(74) *Attorney, Agent, or Firm*—Ladas and Parry LLP

(57) ABSTRACT

The present invention relates to novel 2-fluoro-pyrrolo[2,1-c][1,4]benzodiazepine dimers useful as antitumour agents and to a process for the preparation thereof.

29 Claims, No Drawings

C2-FLUORO PYRROLO [2,1-C][1,4]BENZODIAZEPINE DIMERS

FIELD OF THE INVENTION

The present invention relates to novel 2-fluoro-pyrrolo[2,1-c][1,4]benzodiazepine dimers useful as potential antitumour agents. The present invention also relates to a process for the preparation of novel 2-fluoro-pyrrolo[2,1-c][1,4] benzodiazepine dimes useful as potential antitumour agents. The present invention particularly relates to a process for the preparation of new bis-2-fluoro-pyrrolo[2,1-c][1,4]benzodiazepines useful as anticancer agents. More particularly, it provides a process for the preparation of 1,1'-{[(bisalkane-1,N-diyl)]dioxy}bis[(11aS)-2-fluoro-7-metoxy-1,2,3,11a-terahydro-5H-pyrrolo [2,1-c][1,4]benzodiazepin-5-one, with aliphatic chain length variations for the compounds and also describes the anticancer (antitumour) activity. The structural formula of novel bis-2-fluoro-pyrrolo[2,1-c][1,4] benzodiazepine is as follows, wherein n=3, 4, 5, 6, 7, 8, 9, 10.

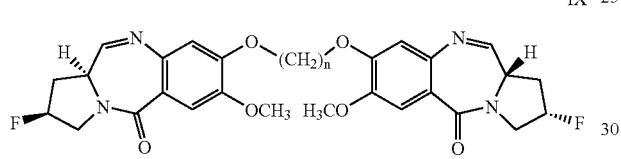

IX

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These PBDs are a family of sequence selective DNA-binding antitumour antibiotics that bind exclusively to the exocyclic N2-guanine in the minor groove of DNA via an acid-labile aminal bond to the electophilic imine at the N10-C11 position. (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W.; Speous, C. L. *J. Mol. Biol.*, 1970, 51, 551.; Hurley, L. H. Gairpla, C.; Zmijewski, M. *Biochem. Biophys. Acta.*, 1977, 475, 521.; Kaplan, D. J.; Hurley, L. H. *Biochemistry*, 1981, 20, 7572.) All biologically active PBDs possess the (S) configuration at the chiral C11a position which provides the molecule with a right-handed twist, which allows them to follow the curvature of the minor groove of B-form double-stranded DNA spanning three base pairs. Recently, PBD dimers have been developed that comprise two C2-exo-methylene-substituted DC-81 subunits tethered through their C-8 position via an inert propanedioxy linker. (Gregson, S. J.; Howard, P. W.; Hartely, J. A.; Brooks N. A.; Adams, L. J.; Jenkins, Kelland, L. R.; Thurston, D. E. *J. Med. Chem.*, 2001, 44, 737.). A recent development has been the linking of two PBD units through their C-8 positions to give bisfunctional alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S.; Hurley, L. H. *J. Org. Chem.*, 1996, 61, 8141–8147). Recently, noncross-linking mixed imine-amide PBD dimers have been synthesized that have significant DNA binding ability and potent anti-tumour activitiy (Kamal A.; Laxman, N.; Ramesh, G.; Ramulu, P.; Srinivas, U.S. Pat. No. 636,233; Kamal, A.; Ramesh, G.; Laxman, N.; Ramulu, P.; Srinivas, O.; Neelima, K.; Kondapi, A. K.; Srinu, V. B.; Nagarajaram, H. M. *J. Med. Chem.* 2002, 45, 4679.).

PBDs are of considerable current interest due to their ability to recognize and subsequently form covalent bonds to specific base sequences of double-stranded DNA. Naturally occurring pyrrolo[2,1-c][1,4]benzodiazepines belong to a group of antitumour antibiotics derived from *Streptomyces* species with family members including anthramycin, tomaymycin, sibiromycin, chicamycin, neothramycins A and B, and DC-81.

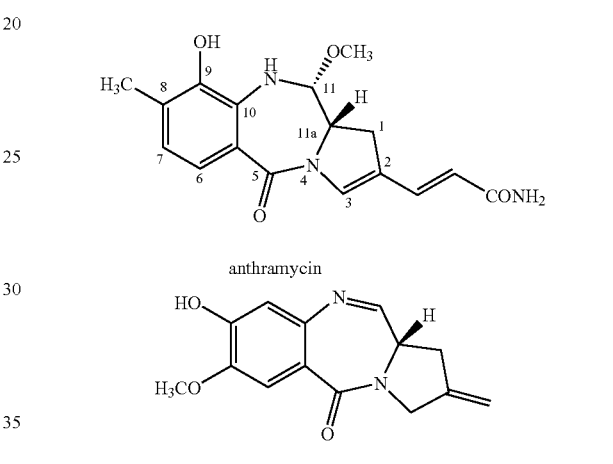

anthramycin

C2-exo-methylene-substimted DC-81

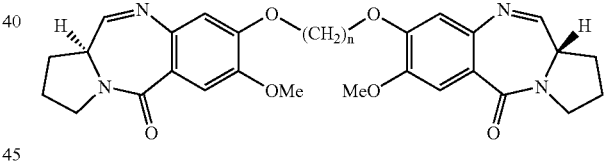

DC-81 dimmers (n=3–5); DSB-120 (n=3)

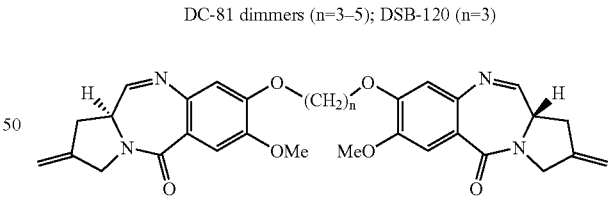

SJG-136

However, the clinical efficacy for these antibiotics is hindered by several limitations, such as poor water solubility and cardiotoxicity and development of drug resistance and metabolic inactivation.

OBJECT OF THE INVENTION

The main object of the invention is to provide new bis-2-fluoro pyrrolo[2,1-c][1,4]benzodiazepines useful as antitumour agents.

Another object of the invention is to provide a process for the preparation of novel fluoro pyrrolo[2,1-c][1,4]benzodiazepines useful as antitumour agents.

SUMMARY OF THE INVENTION

According the present invention provides fluoro pyrrolo [2,1-c][1,4]benzodiazepine dimers of formula IX where n is 3 to 10.

Formula IX

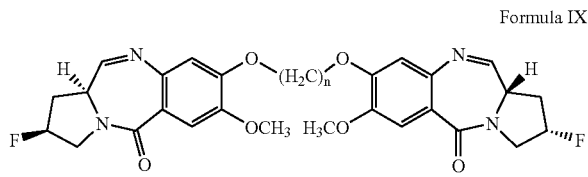

In one embodiment of the invention, the compound of formula IX is 1,1'-{[(propane-1,3-diyl)dioxy]bis[(11aS)-2-fluoro-7-methoxy-1,2,3,11a-tetra-hydro-5H-pyrrolo[2,1-c][1,4]benzodiazepin-5-one]}.

In another embodiment of the invention, the compound of formula IX is 1,1'-{[(butane-1,4-diyl)dioxy]bis[(11aS)-2-fluoro-7-methoxy-1,2,3,11a-tetra-hydro-5H-pyrrolo[2,1-c][1,4]benzodiazepin-5-one]}.

In another embodiment of the invention, the compound of formula IX is 1,1'-{[(pentane-1,5-diyl)dioxy]bis[(11aS)-2-fluoro-7-methoxy-1,2,3,11a-tetra-hydro-5H-pyrrolo[2,1-c][1,4]benzodiazepin-5-one]}.

The present invention also provides a process for the preparation of bis 2-fluoro pyrrolo[2,1-c][1,4]benzodiazepines of formula IX.

Formula IX

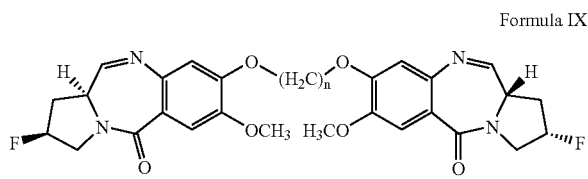

where n is 3 to 10, which comprises:

(a) reacting methyl (2S)-N-[4-benzyloxy-5-methoxy-2-nitrobenzoyl]-4-hydroxypyrrolidine-2-carboxylate dissolved in an organic solvent;

(b) cooling the solution and adding a solution of diethylaminosulfurtrifluoride (DAST) in an organic solvent drop wise;

(c) isolating the methyl (2S)-N-[4-benzyloxy-5-methoxy-2-nitrobenzoyl]-4-fluoropyrrolidine-2carboxylate with DIBAL-H formed in the presence of an organic solvent and cooling;

(d) isolating methyl (2S)-N-[4-benzyloxy-5-methoxy-2-nitrobenzoyl]-4-fluoropyrrolidine-2-carboxaldehyde formed;

(e) protecting methyl (2S)-N-[4-benzyloxy-5-methoxy-2-nitrobenzoyl]-4-fluoropyrrolidine-2-carboxaldehyde with EtSH in presence of an organic solvent;

(f) isolating (2S)-N-[4-benzyloxy-5-methoxy-2-nitrobenzoyl]-4-fluoropyrrolidine-2-carboxaldehyde diethylthioacetal;

(g) reacting the (2S)-N-[4-benzyloxy-5-methoxy-2-nitrobenzoyl]-4-fluoropyrrolidine-2-carboxaldehyde diethylthioacetal with a debenzylating agent to obtain (2S)-N-[4-hydroxy-5-methoxy-2-nitrobenzoyl]-4-fluoropyrrolidine-2-carboxaldehyde-diethylthioacetal of formula VI, Formula VI

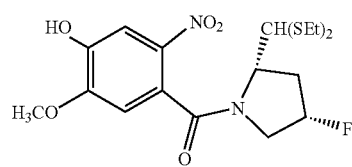

(h) reacting (2S)-N-[4-hydroxy-5-methoxy-2-nitrobenzoyl]-4-fluoro-2-carboxaldehyde diethylthioacetal of formula VI with a dibromoalkane in an aprotic water miscible organic solvent and in the presence of a mild inorganic base up to refluxing temperature and isolating 1,1'-{[(alkane-1,N-diyl)dioxy}bis[(2-nitro-5-methoxy-1,4-phenylene)carbonyl]bis[4-fluoropyrrolidin-2-carboxaldehyde diethylthioacetal] of formula VII where n is 3–10

Formula VII

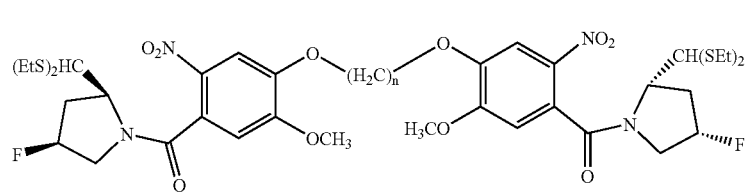

(i) reducing the compound of formula VII with SnCl$_2$.2H$_2$O in presence of organic solvent up to a reflux temperature and isolating 1,1'-{[(alkane-1,N-diyl)dioxy}bis[(2-amino-5-methoxy-1,4-phenylene)carbonyl]]bis[4-fluoro-pyrrolidin-2-carboxaldehyde diethylthioacetal]] of formula VIII where n is 3–10

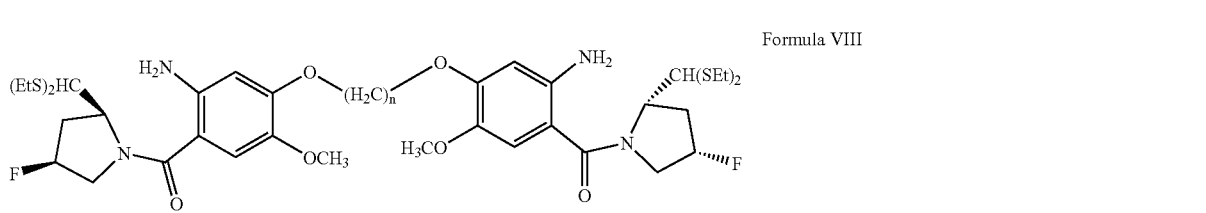

Formula VIII (j) reacting the compound of formula VIII with a deprotecting agent to obtain bis 2-fluoro pyrrolo[2,1-c][1,4]benzodiazepines of formula IX wherein n is as stated above.

In one embodiment of the invention, the organic solvent used in steps (a), (b) and (c) comprises CH$_2$Cl$_2$.

In another embodiment of the invention, in step (a) the solution is cooled to a temperate of –78° C.

In another embodiment of the invention, the drop wise addition in step (b) is carried out for a period of 40 min.

In another embodiment of the invention, step (c) is carried out after 15 hours of step (b).

In yet another embodiment of the invention, the cooling in step (c) is done to a temperature of –78° C. and for a period of 45 minutes.

In another embodiment of the invention, step (e) is carried out in presence of an organic solvent and at room temperature.

In yet another embodiment of the invention, the (2S)-N-[4-hydroxy-5-methoxy-2-nitrobenzoyl]-4-fluoro-2-carboxaldehyde diethylthioacetal of formula VI is reacted with a dibromoalkane in an aprotic water miscible organic solvent selected from the group consisting of acetone, acetonitrile and DMF and in the presence of a mild inorganic base selected from the group consisting of K$_2$CO$_3$, CsCO$_3$ and BaCO$_3$.

In another embodiment of the invention, step (h) is carried out for a period of about 48 hours.

In another embodiment of the invention, the reduction in step (i) is carried out in the presence of an organic solvent comprising methanol.

In yet another embodiment of the invention, the deprotecting agent comprises a combination of HgCl$_2$ and HgO in CH$_3$CN/H$_2$O.

The present invention also provides a process for the preparation of bis 2-fluoro pyrrolo[2,1-c][1,4]benzodiazepines of formula IX

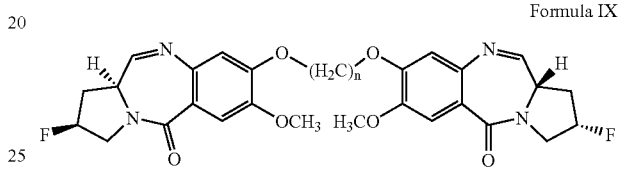

Formula IX where n is 3 to 10, which comprises:
(a) (2S)-N-[4-hydroxy-5-methoxy-2-nitrobenzoyl]-4-fluoropyrrolidine-2-carboxaldehyde-diethylthioacetal of formula VI,

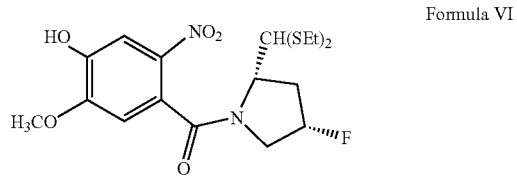

Formula VI (b) reacting (2S)-N-[4-hydroxy-5-methoxy-2-nitrobenzoyl]-4-fluoro-2-carboxaldehyde diethylthioacetal of formula VI with a dibromoalkane in an aprotic water miscible organic solvent and in the presence of a mild inorganic base up to refluxing temperature and isolating 1,1'-{[(alkane-1,N-diyl)dioxy}bis[(2-nitro-5-methoxy-1,4-phenylene) carbonyl]bis[4-fluoropyrrolidin-2-carboxaldehyde diethylthioacetal] of formula VII where n is 3–10

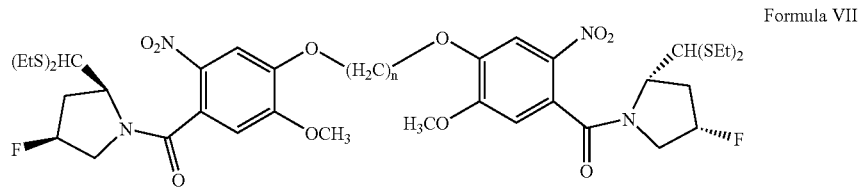

Formula VII (c) reducing the compound of formula VII with SnCl$_2$.2H$_2$O in presence of organic solvent up to a reflux temperature and isolating 1,1'-{[(alkane-1,N-diyl)dioxy}bis[(2-amino-5-methoxy-1,4-phenylene)carbonyl]]bis[4-fluoro-pyrrolidin-2-carboxaldehyde diethylthioacetal)]] of formula VIII where n is 3–10

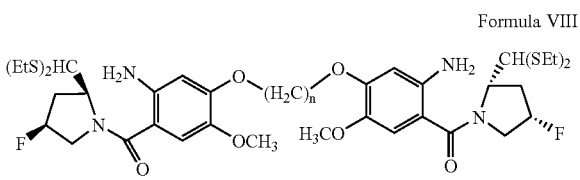

Formula VIII (d) reacting the compound of formula VIII with a deprotecting agent to obtain bis 2-fluoro pyrrolo[2,1-c][1,4] benzodiazepines of formula IX wherein n is as stated above.

In yet another embodiment of the invention, the (2S)-N-[4-hydroxy-5-methoxy-2-nitrobenzoyl]-4-fluoro-2-carboxaldehyde diethylthioacetal of formula VI is reacted with a dibromoalkane in an aprotic water miscible organic solvent selected from the group consisting of acetone, acetonitrile ad DMF and in the presence of a mild inorganic base selected from the group consisting of $K_2CO_3$, $CsCO_3$ and $BaCO_3$.

In another embodiment of the invention, step (b) is carried out for a period of about 48 hours.

In another embodiment of the invention, the reduction in step (c) is carried out in the presence of an organic solvent comprising methanol.

In yet another embodiment of the invention, the deprotecting agent comprises a combination of $HgCl_2$ and HgO in $CH_3CN/H_2O$.

DETAILED DESCRIPTION OF THE INVENTION

The present process provides a process for the preparation of bis 2-fluoro pyrrolo[2,1-c][1,4benzodiazepines of formula IX as given above where n is 3 to 10 which comprises reacting (2S)-N-[4-hydroxy-5-methoxy-2-nitrobenzoyl]-4-fluoro-2-carboxaldehyde diethylthioacetal of formula VI with a dibromoalkane in an aprotic water miscible organic solvents. The solvent is preferably chosen from acetone, acetonitrile, and DMF. The reaction is also carried out in the presence of a mild inorganic bases such as $K_2CO_3$, $CsCO_3$ and $BaCO_3$ and up to refluxing temperature for a period of 48 hours. The 1,1'-{[(alkane-1,N-diyl)dioxy}bis[(2-nitro-5-methoxy-1,4-phenylene) carbonyl]bis[4-fluoropyrrolidin-2-carboxaldehyde diethylthioacetal] of formula VII formed where n is 3–10 is then isolated by conventional methods and reduced with $SnCl_2.2H_2O$ in presence of organic solvent up to a reflux temperature. The 1,1'-{[(alkane-1,N-diyl)dioxy}bis[(2-amino-5-methoxy-1,4-phenylene)carbonyl]]bis[4-fluoro-pyrrolidin-2-carboxaldehyde diethylthioacetal]] of formula VIII formed where n is 3–10 is then isolated by known methods. The compound of formula VIII is then reacted with a known deprotecting agent in a conventional manner to obtain the novel bis 2-fluoro pyrrolo[2,1-c][1,4] benzodiazepines of formula IX wherein n are as stated above.

In the alternate, the process comprises first reacting methyl (2S)-N-[4-benzyloxy-5-methoxy-2-nitrobenzoyl]-4-hydroxypyrrolidine-2-carboxylate dissolved in an organic solvent such as $CH_2Cl_2$ and cooling the solution to $-78°$ C. To this cooled solution, a solution of diethylaminosulfurtrifluoride (DAST) in an organic solvent such as $CH_2Cl_2$ is added drop wise over a period of 40 min. After 15 hours methyl (2S)-N-[4-benzyloxy-5-methoxy-2-nitrobenzoyl]-4-fluoropyrrolidine-2-carboxylate of formula II with DIBAL-H formula III is isolated and then cooled in the presence of organic solvent such as $CH_2Cl_2$ $-78°$ C. for a period of 45 min. The methyl (2S)-N-[4-benzyloxy-5-methoxy-2-nitrobenzoyl]-4-fluoropyrrolidine-2-carboxaldehyde formed is isolated by conventional methods and protected with EtSH in the presence of organic solvent at room temperature. The (2S)-N-[4-benzyloxy-5-methoxy-2-nitrobenzoyl]-4-fluoropyrrolidine-2-carboxaldehyde diethylthioacetal obtained is then isolated by known methods and reacted with any conventional debenzylating agent to give (2S)-N-[4-hydroxy-5-methoxy-2-nitrobenzoyl]-4-fluoropyrrolidine-2-carboxaldehyde-diethylthioacetal of formula VI. The compound of formula VI is then converted to the compound of formula IX in the manner indicated above.

The precursor, methyl (2S)-N-(4-benzyloxy-5-methoxy-2-nitrobenzoyl)-4-hydroxypyrrolidine-2-carboxylate (intermediates of DC-81) was prepared by literature methods (Thurston, D. E.; Murthy, V. S.; Langley, D. R.; Jones, G. B. *Synthesis*, 1990, 81.)

Some representative compounds of formula IX of present invention are given below:

1) 1,1'-{[(propane-1,3-diyl)dioxy]bis[(11aS)-2-fluoro-7-methoxy-1,2,3,11a-tetra-hydro-5H-pyrrolo[2,1-C][1,4] benzodiazepin-5-one]}
2) 1,1'-{[(butane-1,4-diyl)dioxy]bis[(11aS)-2-fluoro-7-methoxy-1,2,3,11a-tetra-hydro-5H-pyrrolo[2,1-c][1,4] benzodiazepin-5-one]}
3) 1,1'-{[(pentane-1,5-diyl)dioxy]bis[(11aS)-2-fluoro-7-methoxy-1,2,3,11a-tetra-hydro-5H-pyrrolo[2,1-c][1,4] benzodiazepin-5-one]}

The reaction scheme is given below:

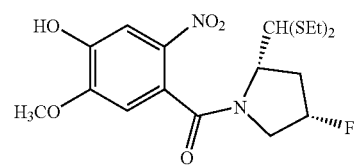

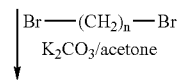

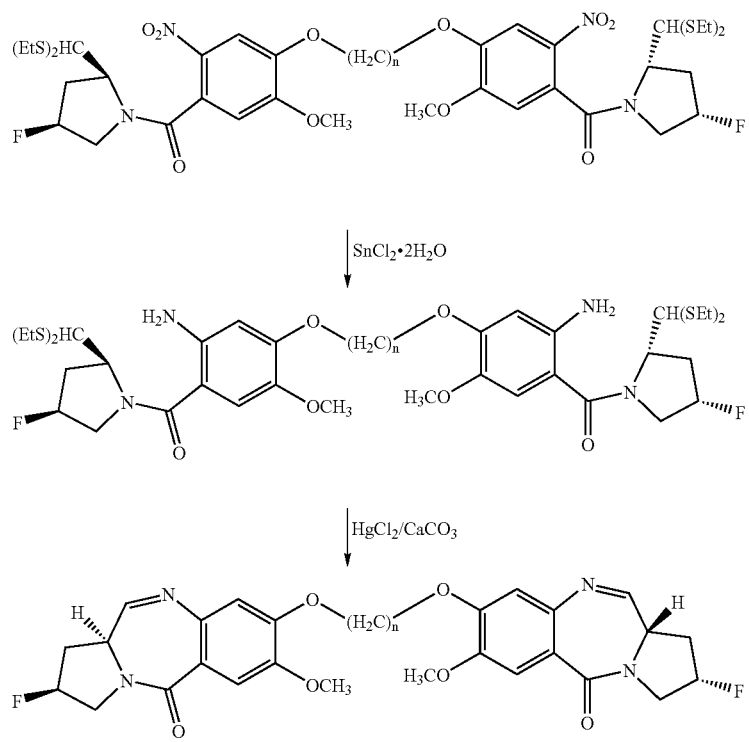

These new analogues of pyrrolo[2,1-c][1,4]benzodiazepine dimers substituted at C-2 position have shown promising anticancer activity in various cell lines. The molecules synthesized are of immense biological significance with potential sequence selective DNA-binding property. This resulted in design and synthesis of new congeners, which comprise:
1. The fluoro substitution at C-2 position of DC-81 intermediates.
2. The ether linkage between two fluoro DC-81 monomers at C-8 position.
3. Refluxing the reaction mixture for 24–48 h.
4. Synthesis of fluoro PBD antitumour antibiotic dimer imines.
5. Purification by column chromatography using different solvents like ethylacetate, hexane, dichloromethane and methanol.

Representative compounds of Formula IX include

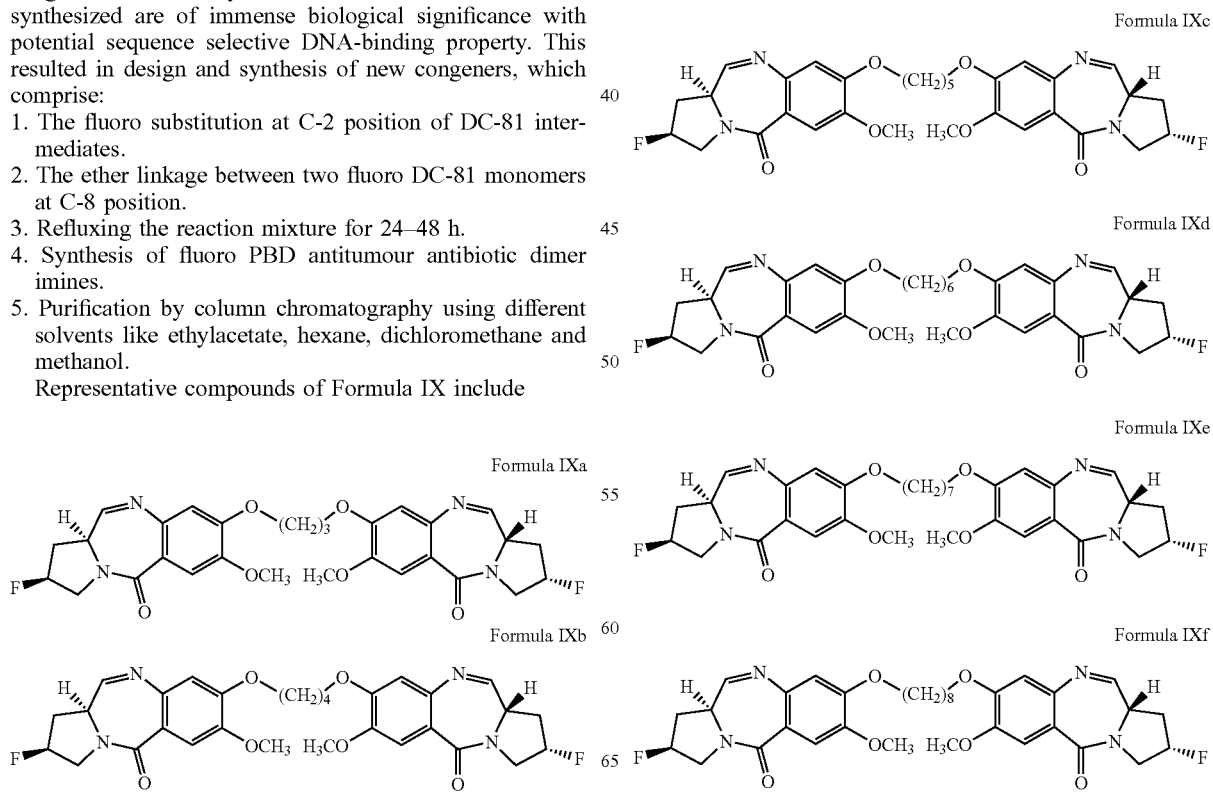

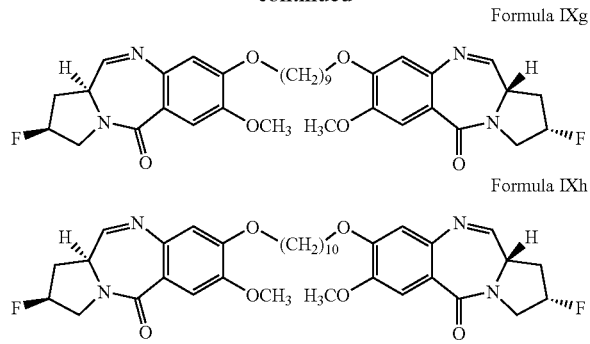

Formula IXg

Formula IXh

The following examples are given by way of illustration and therefore should not be construed to the present limit of the scope of invention.

EXAMPLE 1

A solution of (2S)-N-(4-hydroxy-5-methoxy-2-nitrobenzoyl)-4-fluoro pyrrolidine 2-carboxaldehyde diethylthioacetal VI (418 mg, 1 mmol), 1,3-dibromopropane (101 mg, 0.5 mmol) and $K_2CO_3$ (414 mg, 3 mmol) in dry acetone (40 ml) was refluxed for 48 h. After the completion of reaction as indicated by TLC, EtOAc-hexane (7:3), the reaction mixture was poured on to the water and then extracted with ethylacetate. Evaporation of the organic layer gave the crude product, which was further purified by column chromatography on silica gel eluting with EtOAc-hexane (1:1) to give the pure 1,1'-{[(Propane-1,3 diyl)dioxy]bis[2-nitro-5-methoxy-1,4-phenylene)carbonyl]}bis[4-fluoro pyrrolidine-2-carboxaldehyde diethylthioacetal] VII. $H^1$ NMR ($CDCl_3$, 200 MHz): δ 1.2–1.39 (m, 12H), 2.4–2.68 (m, 6H), 2.7–2.9 (m, 8H), 3.41–3.62 (m, 4H), 3.99 (s, 6H), 4.29–4.4 (m, 4H), 4.52 (d, j=3.9 Hz, 2H), 4.69–4.79 (m, 2H), 5.05 (t, 1H), 6.85 (s, 2H), 7.63 (s, 2H). FAB MASS: 877 (M+H)

1,1'-{[(propane-1,3diyl)dioxy]bis[2-nitro-5-methoxy-1,4-phenylene)carbonyl]}bis[4-fluoro pyrrolidine-2-carboxaldehyde diethyl thioacetal] VII (876 mg, 1.0 mmol) was dissolved in methanol (10 mL) and to this was added $SnCl_2.2H_2O$ (1.124 g, 5.0 mmol) and was refluxed for 1.5 h. The reaction mixture was then carefully adjusted to pH 8 with saturated $NaHCO_3$ solution and then extracted with ethyl acetate (3×20 mL). The combined organic phase was dried over $Na_2SO_4$ and evaporated under vacuum to afford the crude 1,1'-{[(Propane-1,3 diyl)dioxy]bis[2-amino-5-methoxy-1,4-phenylene) carbonyl]}bis[4-fluoro pyrrolidine-2-carboxaldehyde diethyl thioacetal].

A solution of the 1,1'-{[(propane-1,3 diyl)dioxy]bis[2-amino-5-methoxy-1,4-phenylene)carbonyl]}bis[4-fluoro pyrrolidine-2-carboxaldehyde diethylthioacetal] VIII (846 mg, 1 mmol), $HgCl_2$ (794 mg, 2.93 mmol) and HgO (686 mg, 3.18 mmol) in $CH_3CN/H_2O$ (3:1, 15 ml) was stirred at room temperature for 12 h until TLC (EtOAc), indicated complete loss of starting material. Then organic layer is evaporated in vacuum and the residue is diluted with EtOAc. To this, saturated $NaHCO_3$ solution was added slowly at room temperature and the mixture was filtered through celite and washed with ethylacetate. The filtrate was evaporated in vacuum to get crude 1,1'-{[(propane-1,3-diyl)]dioxy}bis[(11aS)-2-fluoro-7-methoxy-1,2,3,11a-tetrahydro-5H-pyrrolo[2,1-c][1,4 benzodiazepin-5-one] of formula IXa, which was further purified by column chromatography on silica gel eluting first with ethyl acetate to remove traces of mercuric salts and further eluted with $CHCl_3$-methanol (8.5:1.5). $H^1$ NMR ($CDCl_3$, 200 MHz): δ 2.15–2.45 (m, 6H), 3.7–3.9 (m, 6H), 4.01(s, 6H), 4.22–4.3 (m, 4 H), 5.05 (t, 1H), 5.20 (t, 1H), 6.80 (s, 2H), 7.42 (s, 2H), 7.80 (d, 2H, J=4.2 Hz). FAB MASS: 569 (M+H)

EXAMPLE 2

A solution of (2S)-N-(4-hydroxy-5-metoxy-2-nitrobenzoyl)-4-fluoro pyrrolidine 2-carboxaldehyde diethylthioacetal VI (418 mg, 1 mmol), 1,4-dibromobutane (107 mg, 0.5 mmol) and $K_2CO_3$ (414 mg, 3 mmol) in dry acetone (20 ml) was refluxed for 48 h. After the completion of reaction as indicated by TLC, EtOAc-hexane (7:3), the reaction mixture was poured on to the water and then extracted with ethyl acetate. Evaporation of the organic layer gave the crude product, which was purified by column chromatography on silica gel eluting with EtOAc-hexane (1:1) to give the pure 1,1'-{[Butane-1,4-diyl)dioxy]bis(2-nitro-5-methoxy-1,4-phenylene)carbonyl]}bis[4-fluoro pyrroilidine-2-carboxaldehyde diethylthioacetal] VII. $H^1$ NMR ($CDCl_3$, 200 MHz): δ 1.29–1.4 (m, 12H), 2.1–2.2 (m, 4H), 2.49–2.61 (m, 4H), 2.7–2.9 (m, 8H), 3.4–3.7 (m, 4H), 3.92 (s, 6H), 4.27 (t, 4 H), 4.58 (d, 2H), 4.70–4.85 (m, 2H), 5.08 (t, 1H), 5.29 (t, 1H), 6.82 (s, 2H), 7.65 (s, 2H). FAB MASS: 891 (M+H)

1,1'-{[Butane-1,4-diyl)dioxy]bis(2-nitro-5-methoxy-1,4-phenylene)carbonyl]}bis[4-fluoro pyrrolidine-2-carboxaldehyde diethylthioacetal] of formula VII (890 mg, 1.0 mmol) was dissolved in methanol (10 ml) and added $SnCl_2.2H_2O$ (1.124 g, 5.0 mmol) was refluxed for 1.5 h. The reaction mixture was then carefully adjusted to pH 8 with saturated $NaHCO_3$ solution and then extracted with ethyl acetate (3×20 ml). The combined organic phase was dried over $Na_2SO_4$ and evaporated under vacuum to afford the crude of pure 1,1'-{[Butane-1,4-diyl)dioxy]bis(2-amino-5-methoxy-1,4-phenylene)carbonyl]}bis[4-fluoropyrrolidine-2-carboxaldehyde diethylthioacetal of formula VIII.

A solution of 1,1'-{[Butane-1,4-diyl)dioxy]bis(2-amino-5-methoxy-1,4-phenylene)carbonyl]}bis[4-fluoropyrrolidine-2-carboxaldehyde diethylthioacetal of formula VIII (861 mg, 1 mmol), $HgCl_2$ (794 mg, 2.93 mmol) and HgO (687 mg, 3.18 mmol) in $CH_3CN/H_2O$ (3:1, 15 ml) was stirred at room temperature for 12 h until TLC (EtOAc), indicted complete loss of starting material. Then organic layer was evaporated in vacuum and the residue is diluted with EtOAc. To this, saturated $NaHCO_3$ solution was added slowly at room temperature and the mixture is filtered through celite and washed with ethyl acetate. The filtrate was evaporated in vacuum to get crude 1,1'-{[(butane-1,4-diyl)]dioxy}bis[(11aS)-2-fluoro-7-methoxy-1,2,3,11a-tetrahydro-5H-pyrrolo[2,1-c][1,4]benzodiazepin-5-one IXb, which was further purified by column chromatography on silica gel eluting first with ethylacetate to remove traces of mercuric salts and further eluted with $CHCl_3$-methanol (9:1). $H^1$ NMR ($CDCl_3$, 200 MHz): δ 1.94–2.09 (m, 4H), 2.1–2.5 (m, 4H), 3.5–3.82 (m, 6H), 3.98 (s, 6H), 4.1–4.37 (m, 4H), 5.29 (t, 1H), 5.5 (t, 1H), 6.80 (s, 2H), 7.45 (s, 2H), 7.80 (d, 2H, J=4.3 Hz). FAB MASS: 583 (M+H)

EXAMPLE 3

A solution of (2S)-N-(4-hydroxy-5-methoxy-2-nitrobenzoyl)-4-fluoro pyrrolidine 2-carboxaldehyde diethylthioacetal VI (418 mg, 1 mmol), 1,5-dibromopentane (114 mg, 0.5 mmol) and $K_2CO_3$ (414 mg, 3 mmol) in dry acetone (20 ml) was refluxed for 48 h. After the completion of reaction as indicated by TLC, EtOAc-hexane (7:3), the reaction mixture was poured on to the water and then extracted with ethylacetate. Evaporation of the organic layer gave the crude product, which was further purified by column chromatography on silica gel eluting with EtOAc-hexane (1:1) to give the pure 1,1'-{[Pentane-1,5-diyl)dioxy]bis(2-nitro-5-methoxy-1,4-phenylene) carbonyl]}bis[4-fluoro pyrroilidine-2-carboxaldehyde diethyl thioacetal VII. $H^1$ NMR ($CDCl_3$, 200 MHz): δ 1.2–1.42 (m, 12H), 1.65–2.1 (m, 6H), 2.4–2.61 (m, 4H), 2.7–2.91 (m, 8H), 3.29–3.67 (m, 4H), 3.99 (s, 6H), 4.09–4.25 (m, 4H), 4.52–4.68 (m, 2H), 4.82 (d, 2H), 5.10 (t, 1H), 5.32 (t, 1H), 6.89 (s, 2H), 7.69 (s, 2H). FAB MASS: 905 (M+H)

1,1'-{[Pentane-1,5-diyl)dioxy]bis(2-nitro-5-methoxy-1,4-phenylene)carbonyl]}bis[4-fluoro pyrroilidine-2-carboxaldehyde diethylthioacetal] of formula VII (905 mg, 1.0 mmol) was dissolved in methanol (10 ml) and to it was added $SnCl_2.2H_2O$ (1.124 g, 5.0 mmol) and was refluxed for 1.5 h. The reaction mixture was then carefully adjusted to pH 8 with saturated $NaHCO_3$ solution and then extracted with ethyl acetate (3×20 ml). The combined organic phase was dried over $Na_2SO_4$ and evaporated under vacuum to afford the crude 1'-{[Pentane-1,5-diyl)dioxy]bis(2-amino-5-methoxy-1,4-phenylene)carbonyl]}bis[4-fluoropyrrolidine-2-carboxaldehyde diethyl thioacetal of formula VIII.

A solution of 1,1'-{[Pentane-1,5-diyl)dioxy]bis(2-amino-5-methoxy-1,4-phenylene)carbonyl]}bis[4-fluoropyrrolidine-2-carboxaldehyde diethylthioacetal of formula VIII (875 mg, 1 mmol), $HgCl_2$ (794 mg, 2.93 mmol) and HgO (687 mg, 3.18 mmol) in $CH_3CN/H_2O$ (3:1, 15 ml) was stirred at room temperature for 12 h until TLC (EtOAc) indicated complete loss of starting material. Then organic layer was evaporated in vacuum and the residue was diluted with EtOAc. To this, saturated $NaHCO_3$ solution was added slowly at room temperature and the mixture was filtered through celite and washed with ethylacetate. The filtrate was evaporated in vacuum to get crude 1,1'-{[(pentane-1,5-diyl)]dioxy}bis[(11aS)-2-fluoro-7-methoxy-1,2,3,11a-tetrahydro-5H-pyrrolo[2,1-c][1,4]benzodiazepin-5-one IXc, which was further purified by column chromatography on silica gel eluting first with ethylacetate to remove traces of mercuric salts and further eluted with $CHCl_3$-methanol (9:1). $H^1$ NMR ($CDCl_3$, 200 MHz): δ 1.58–1.81 (m, 4H), 1.90–2.01 (m, 2H), 2.38–2.50 (m, 4H), 3.08–3.2 (m, 4H), 4.01–4.20 (m, 4H), 4.92 (s, 6H), 5.21 (t, 1H), 5.5 (t, 1H), 6.81 (s, 2H), 7.49 (s, 2H), 7.83 (d, 2H, J=4.4 Hz). FAB MASS: 597 (M+H)

Biological Activity: In vitro biological activity studies were carried out at National Cancer Institute (USA).

Cytotoxicity: Compounds IXa and IXc were evaluated for in vitro against sixty human tumour cells derived from nine cancer types (leukemia, non-small-cell lung, colon, CNS, melanoma, ovarian, prostate, and breast cancer). For each compound, dose response curves against each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI, 0% growth) and 50% cell death (LC50, −50% growth) compared with the control was calculated. The mean graph midpoint values of $\log_{10}$ TGI and $\log_{10}$ LC50 as well as $\log_{10}$ GI50 for IXa and IXc are listed in Table 1. As demonstrated by mean graph pattern (Table 4), compound IXc exhibits an interesting profile of activity and selectivity for various cell lines. The mean graph mid point of $\log_{10}$ TGI and $\log_{10}$ LC50 showed similar pattern to the $\log_{10}$ GI50 mean graph mid points.

TABLE 1

$\log_{10}$ GI50 $\log_{10}$ TGI and $\log_{10}$ LC50 mean graphs midpoints (MG_MID) of in vitro Cytotoxicity data for the compounds IXa and IXc against human tumour cell lines.

| Compound | $\log_{10}$ GI50 | $\log_{10}$ TGI | $\log_{10}$ LC50 |
|---|---|---|---|
| IXa | −5.21 | −4.75 | −4.31 |
| IXc | −7.14 | −6.27 | −4.87 |

TABLE 2

In vitro one dose primary anticancer assay[a] bisfluorinated PBDs of formula IXa, and IXc

| | Growth percentages | | |
|---|---|---|---|
| PBD | (Lung) NCI-H460 | (Breast) MCF7 | (CNS) SF-268 |
| IXa | 0 | 0 | 0 |
| IXc | 0 | 0 | 0 |

[a]One dose of IXCa and IXc at $10^{-4}$ molar concentration

The anticancer activity for two representative compounds has been given in Table 2. The comparison of the data of Table 3 reveals the importance of the alkane spacer. As the alkane spacer increased from 3–5 the cytotoxic activity has moderately enhanced. The 5 carbon spacer of compound IXc confers a suitable fit in the minor groove of double helix DNA and shows slightly higher activity in this series of compounds IXa and IXc.

TABLE 3

Log GI50 (inhibitory concentration) Values for Compounds IXa, and IXc

| cancer | Compound IXa | Compound IXc |
|---|---|---|
| leukemia | 5.668 | 7.794 |
| non-small-cell lung | 5.258 | 7.318 |
| colon | 5.285 | 7.064 |
| CNS | 5.543 | 7.625 |
| melanoma | 5.490 | 7.301 |
| ovarian | 5.310 | 6.620 |
| renal | 5.315 | 7.492 |
| prostate | 5.180 | 7.430 |
| breast | 5.490 | 7.234 |

Each cancer type represent the average of six to eight different cancer cell lines.

MEAN GRAPH TABLE 4
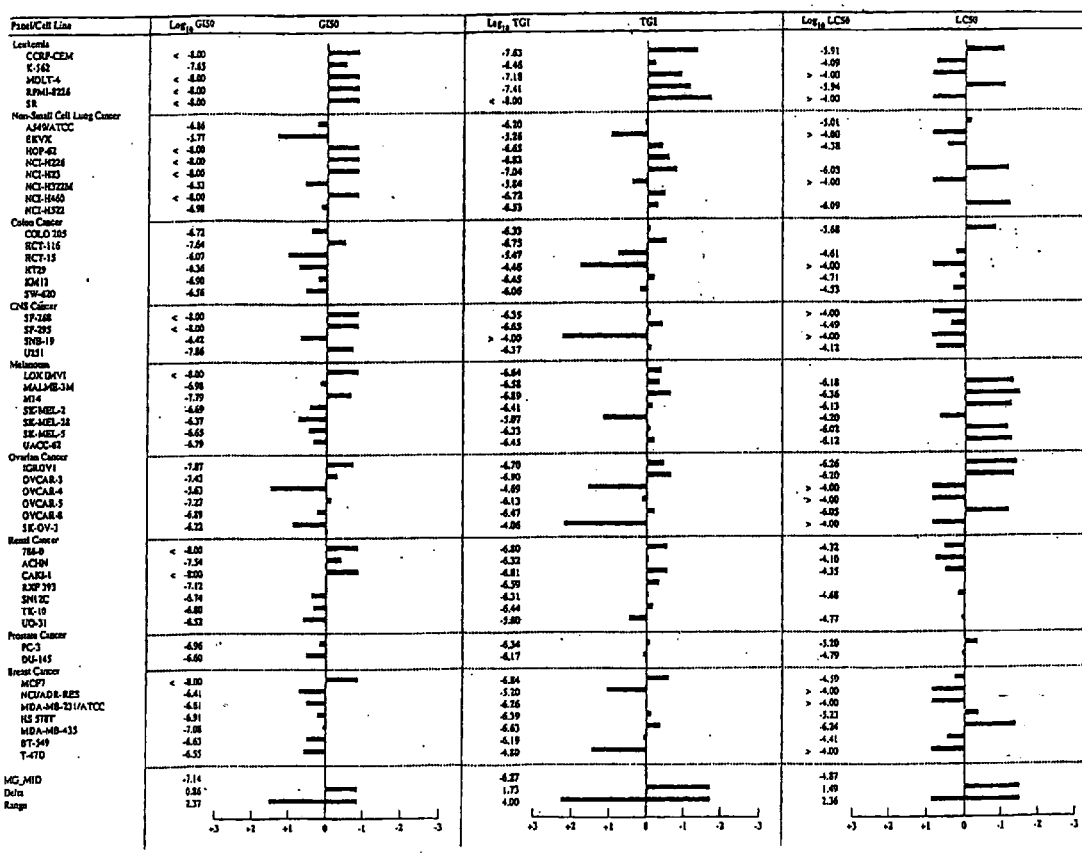

MEAN GRAPH TABLE 4
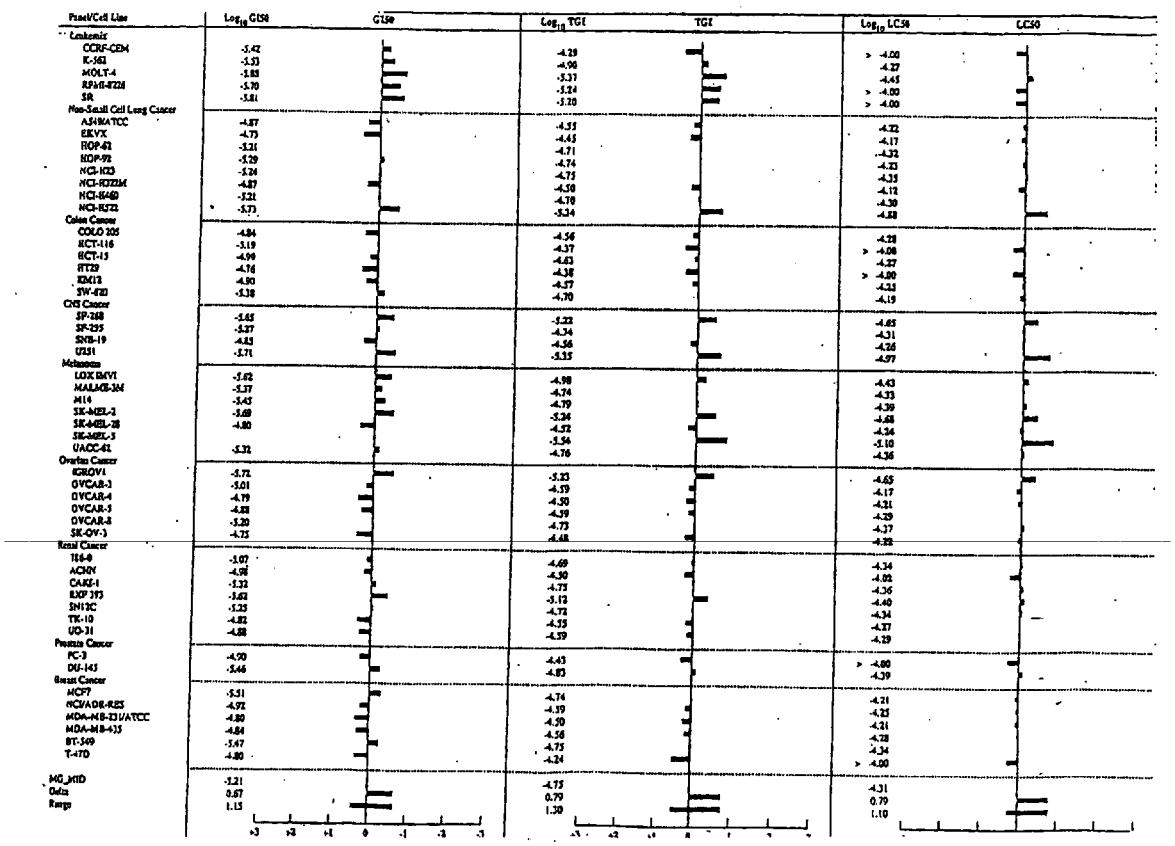

We claim:
1. A compound of formula IX

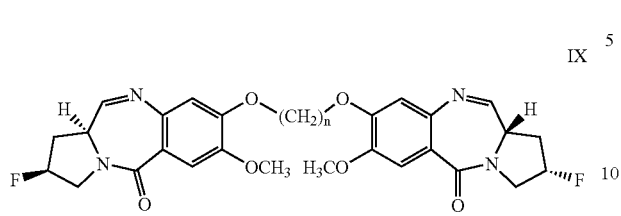

where n is 3 to 10.

2. A compound as claimed in claim 1 of the structure

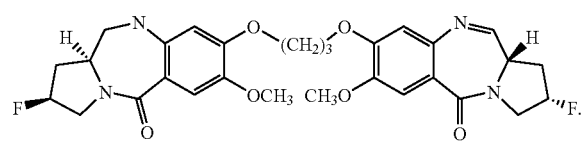

3. A compound as claimed in claim 1 of the structure

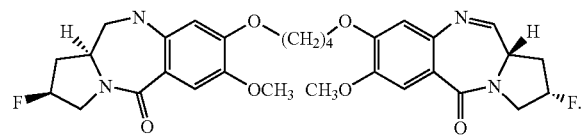

4. A compound as claimed in claim 1 of the structure

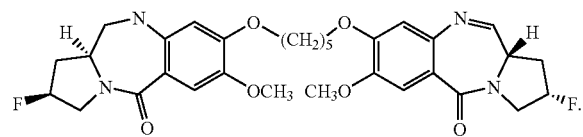

5. A compound as claimed in claim 1 of the structure

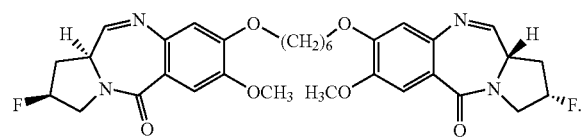

6. A compound as claimed in claim 1 of the structure.

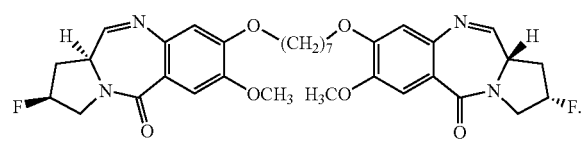

7. A compound as claimed in claim 1 of the structure

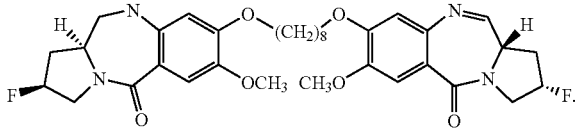

8. A compound as claimed in claim 1 of the structure

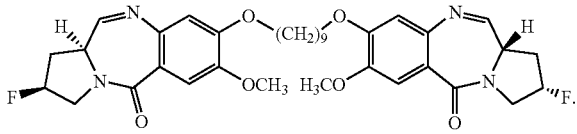

9. A compound A novel pyrrolobenzodiazepine as claimed in claim 1 of the structure

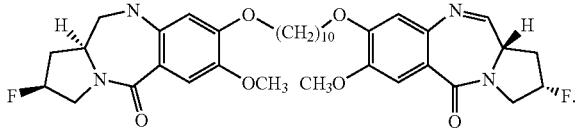

10. A process for the preparation of compound of formula IX

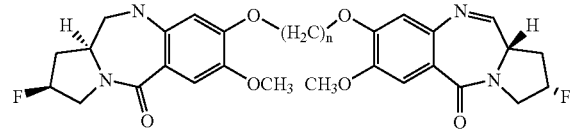

where n is 3 to 10, which comprises:
   (a) reacting methyl (2S)-N-[4-benzyloxy-5methoxy-2-nitrobenzoyl]-4-hydroxypyrrolidine2-carboxylate dissolved in an organic solvent,
   (b) cooling the solution and adding a solution of diethylaminosulfurtrifluoride (DAST) in an organic solvent drop wise;
   (C) isolating the methyl (2S)-N-[4-benzyloxy-5-methoxy-2-nitrobenzoyl]-4-fluoropyrrolidine-2-carboxylate with DIBAL-H formed in the presence of an organic solvent and cooling;
   (d) isolating methyl (2S)-N-[4-benzyloxy-5-methoxy-2-nitrobenzoyl]-4-fluoropyrrolidine-2-carboxaldehyde formed;
   (e) protecting methyl (2S)-N-[4-benzyloxy-5-methoxy-2-nitrobenzoyl]-4-fluoropyrrolidine-2-carboxaldehyde with EtSH in presence of an organic solvent;
   (f) isolating (2S)-N-[4-benzyloxy-5-methoxy-2-nitrobenzoyl]-4-fluoropyrrolidine2-carboxaldehyde diethylthioacetal;
   (g) reacting the (2S)-N-[4-benzyloxy-5-methoxy-2-nitrobenzoyl]-4-fluoropyrrolidine-2-carboxaldehyde diethylthioacetal with a debenzylating agent to obtain (2S)-N-[4-hydroxy-5-methoxy-2-nitrobenzoyl]-4-fluoropyrrolidine-2-carboxaldehyde-diethylthioacetal of formula VI,

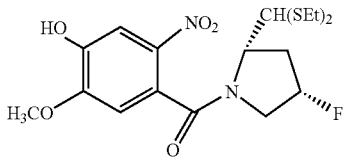

Formula VI (h) reacting (2S)-N-[4-hydroxy-5-methoxy-2-nitrobenzoyl]-4-fluoro-2-carboxaldehyde diethylthioacetal of formula VI with a dibromoalkane in an aprotic water miscible organic solvent and in the presence of a mild inorganic base up to refluxing temperature and isolating 1,1'-{[(alkane-1,N-diyl)dioxy}bis[(2-nitro-5-methoxy-1,4-phenylene)carbonyl]bis [4-fluoropyrrolidin-2-carboxaldehyde diethylthioacetal] of formula VII where n is 3–10

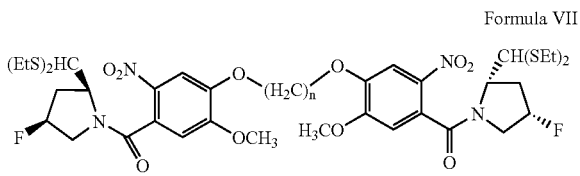

Formula VII (i) reducing the compound of formula VII with SnCl$_2$.2H$_2$O in presence of organic solvent up to a reflux temperature and isolating 1,1'-{[(alkane-1,N-diyl)dioxy}bis[(2-amino-5-methoxy-1,4-phenylene)carbonyl]]bis[4-fluoro-pyrrolidin-2-carboxaldehyde diethylthioacetal]] of formula VIII where n is 3–10

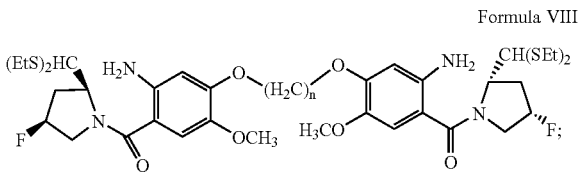

Formula VIII and (j) reacting the compound of formula VIII with a deprotecting agent to obtain bis 2-fluoro pyrrolo[2,1-c][1,4] benzodiazepines of formula IX wherein n is as defined above.

11. A process as claimed in claim 10 wherein the organic solvent used in steps (a), (b) and (c) comprises CH$_2$Cl$_2$.

12. A process as claimed in claim 10 wherein in step (a) the solution is cooled to a temperature of −78° C.

13. A process as claimed in claim 10 wherein the drop wise addition in step (b) is carried out for a period of 40 min.

14. A process as claimed in claim 10 wherein step (c) is carried out 15 hours of step (b).

15. A process as claimed in claim 10 wherein the cooling in step (c) is done to a temperature of −78° C. and for a period of 45 minutes.

16. A process as claimed in claim 10 wherein step (e) is carried out in presence of an organic solvent and at room temperature.

17. A process as claimed in claim 10 wherein the the (2S)-N-[4-hydroxy-5-methoxy-2-nitrobenzoyl]4-fluoro-2-carboxaldehyde diethylthioacetal of formula VI is reacted with a dibromoalkane in an aprotic water miscible organic solvent selected from the group consisting of acetone, acetonitrile and DMF and in the presence of a mild inorganic base selected from the group consisting of K$_2$CO$_3$, CsCO$_3$ and BaCO$_3$.

18. A process as claimed in claim 10 wherein step (h) is carried out for a period of about 48 hours.

19. A process as claimed in claim 10 wherein the reduction in step (i) is carried out in the presence of an organic solvent comprising methanol.

20. A process as claimed in claim 10 wherein the deprotecting agent comprises a combination of HgCl$_2$ and HgO in CH$_3$CN/H$_2$O.

21. A process for the preparation of a compound of formula IX.

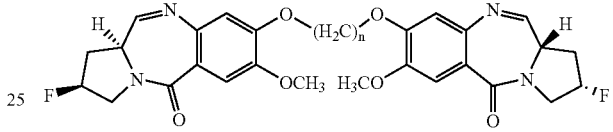

Formula IX where n is 3 to 10, which comprises:

(a) (2S)-N-4-hydroxy-5-methoxy-2-nitrobenzoyl]-4-fluoropyrrolidine-2-carboxaldehyde-diethylthioacetal of formula VI,

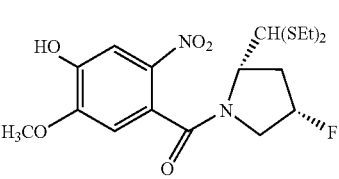

Formula VI (b) reacting (2S)-N-[4-hydroxy-5-methoxy-2-nitrobenzoyl]-4-fluoro-2-carboxaldehyde diethylthioacetal of formula VI with a dibromoalkane in an aprotic water miscible organic solvent and in the presence of a mild inorganic base up to refluxing temperature and isolating 1,1'-{[(alkane-1,N-diyl)dioxy}bis[(2-nitro-5-methoxy-1,4phenylene)carbonyl]bis [4-fluoropyrrolidin-2-carboxaldehyde diethylthioacetal] of formula VII

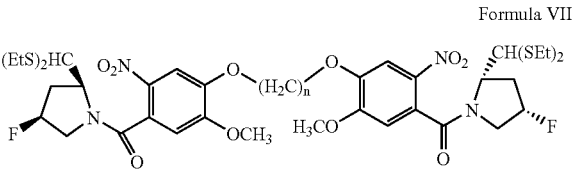

Formula VII where n is 3–10;

(c) reducing the compound of formula VII with SnCl$_2$.2H$_2$O in presence of organic solvent up to a reflux temperature and isolating 1,1'-{[(alkane-1,N-diyl)dioxy}bis[(2-amino-5-methoxy-1,4-phenylene) carbonyl]]bis [4-fluoro-pyrrolidin-2-carboxaldehyde diethylthioacetal]] of formula VIII

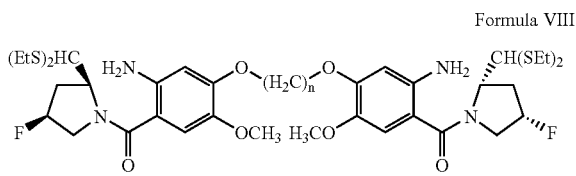

Formula VIII where n is 3–10; and (d) reacting the compound of formula VIII with a deprotecting agent to obtain bis 2-fluoro pyrrolo[2,1-c][1,4] benzodiazepines of formula IX wherein n is as defined above.

22. A process as claimed in claim 21 wherein the (2S)-N-[4-hydroxy-5-methoxy-2-nitrobenzoyl]4-fluoro-2-carboxaldehyde diethylthioacetal of formula VI is reacted with a dibromoalkane in an aprotic water miscible organic solvent selected from the group consisting of acetone, acetonitrile and DMF and in the presence of a mild inorganic base selected from the group consisting of $K_2CO_3$, $CsCO_3$ and $BaCO_3$.

23. A process as claimed in claim 21 wherein step (b) is carried out for a period of about 48 hours.

24. A process as claimed in claim 21 wherein the reduction in step (c) is carried out in the presence of an organic solvent comprising methanol.

25. A process as claimed in claim 21 wherein the deprotecting agent comprises a combination of $HgCl_2$ and HgO in $CH_3CN/H_2O$.

26. A pharmaceutical composition comprising a pharmaceutically effective amount of a compound of formula IX

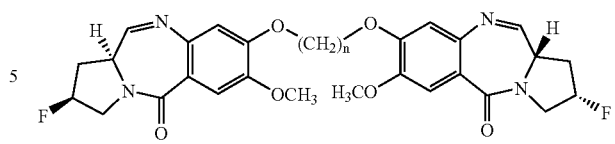

where n is an integer from 3 to 10 and pharmaceutically acceptable additives.

27. A method for the treatment of cancer in a patient need thereof wherein the cancer is selected from the group consisting of leukemia, non-small cell, lung, colon, CNS, melanoma, ovarian, renal, prostate and breast, said method comprising administering to the patient a pharmaceutically effective amount of a compound of formula IX

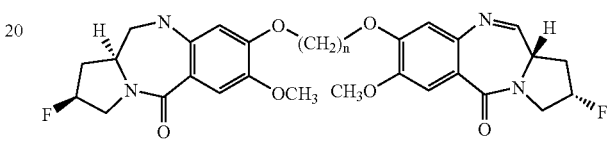

wherein n is an integer of from 3 to 10.

28. A method as claimed in claim 27 wherein the patient is a mammal.

29. A method as claimed in claim 27 wherein the mammal is a human being.

* * * * *